US00PP15359P2

(12) United States Plant Patent
Proud

(10) Patent No.: US PP15,359 P2
(45) Date of Patent: Nov. 23, 2004

(54) ***MANDEVILLA* PLANT NAMED 'MONPROUD'**

(50) Latin Name: *Mandevilla sanderi*
Varietal Denomination: Monproud

(75) Inventor: Andrew Proud, Glendora, CA (US)

(73) Assignee: Monrovia Nursery Co., Azusa, CA (US)

( * ) Notice: Subject to any disclaimer, the term of this patent is extended or adjusted under 35 U.S.C. 154(b) by 0 days.

(21) Appl. No.: 10/775,946

(22) Filed: Feb. 10, 2004

(51) Int. Cl.[7] ..... A01H 5/00
(52) U.S. Cl. ..... Plt./232
(58) Field of Search ..... Plt./232

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Mandevilla* plant named 'Monproud', characterized by its vining plant habit; compact growth habit; short internode; variegated leaves; developing foliage; red and green; fully expanded foliage, pale yellow, green and grayed green; and red purple-colored flowers with yellow-colored throats.

1 Drawing Sheet

Botanical classification/cultivar designation: *Mandevilla sanderi* cultivar Monproud.

BACKGROUND OF THE INVENTION

The present Invention relates to a new and distinct cultivar of *Mandevilla* plant, botanically known as *Mandevilla sanderi*, and hereinafter referred to by the name 'Monproud'.

The new *Mandevilla* is a naturally-occurring branch mutation of the *Mandevilla sanderi* cultivar Red Riding Hood, not patented. The new *Mandevilla* was discovered and selected by the Inventor in August, 1999 in a controlled environment in Azusa, Calif., from within a population of plants of the cultivar Red Riding Hood.

Asexual reproduction of the new cultivar by tissue culture in a laboratory in Azusa, Calif., since September, 2000, has shown that the unique features of this new *Mandevilla* are stable and reproduced true to type in successive generations.

SUMMARY OF THE INVENTION

Plants of the cultivar Monproud have not been observed under all possible environmental conditions. The phenotype may vary somewhat with variations in environment such as temperature and light intensity without, however, any variance in genotype.

The following traits have been repeatedly observed and are determined to be the unique characteristics of 'Monproud'. These characteristics in combination distinguish 'Monproud' as a new and distinct cultivar of *Mandevilla*:

1. Vining plant habit.
2. Compact growth habit, short internodes.
3. Variegated leaves; developing foliage, red and green; fully expanded foliage, pale yellow, green and grayed green.
4. Red purple-colored flowers with yellow-colored throats.

Plants of the new *Mandevilla* are most similar to plants of the parent, the cultivar Red Riding Hood. In side-by-side comparisons conducted in Azusa, Calif., plants of the new cultivar differed from plants of the cultivar Red Riding Hood in the following characteristics:

1. Plants of the new *Mandevilla* were more compact with shorter internodes than plants of the cultivar Red Riding Hood.
2. Leaves of plants of the new *Mandevilla* were variegated whereas leaves of plants of the cultivar Red Riding Hood were solid green in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Mandevilla*.

The photograph at the top of the sheet comprises a side perspective view of a typical plant of 'Monproud' grown in a container.

The photograph at the bottom of the sheet comprises a close-up view of typical flowers and leaves of 'Monproud'.

DETAILED BOTANICAL DESCRIPTION

In the following description, color references are made to The Royal Horticultural Society Colour Chart, 1995 Edition, except where general terms of ordinary dictionary significance are used. Plants used for the above-mentioned photographs and description were about 2.5 years old when the photographs and description were taken. Plants were grown in seven-gallon containers and under commercial production conditions in an outdoor nursery in Azusa, Calif. during the summer. During the production of the plants, day temperatures ranged from 21 to 29° C. and night temperatures ranged from 7 to 16° C.

Botanical classification: *Mandevilla sanderi* cultivar Monproud.

Parentage: Naturally-occurring branch mutation of *Mandevilla sanderi* cultivar Red Riding Hood, not patented.

Propagation:

*Type.*—By cuttings.

*Time to initiate roots on a micro-propagated plant.*—About 45 days.

*Time to produce a rooted micro-propagated plant.*—About 150 days.

*Root description.*—Numerous, fibrous and freely branching; white to tan in color.

Plant description:

*Form.*—Perennial evergreen flowering plant; twining vine. Plants initially upright, then vining and requiring support to maintain upright habit. Plants are typically pinched to enhance lateral branch development; potentially two lateral branches form at every node. Plants compact with short internodes.

*Plant height* (*length*).—About 105 cm.

*Plant diameter, single plant.*—About 46 cm.

*Vigor.*—Moderately vigorous.

*Lateral branches.*—Length: About 100 cm, variable. Diameter: About 6 mm. Internode length: About 6 cm. Shape in cross-section: Round. Strength: Flexible, strong. Texture: Smooth, glabrous. Color: Young stems: 144A. Developing stems: 177B. Fully developed, woody stems: 166B to 166C.

*Foliage description.*—Arrangement: Opposite, simple. Length: About 6 cm. Width: About 3.8 cm. Shape: Elliptic. Apex: Acute. Base: Obtuse. Margin: Entire. Texture, upper and lower surfaces: Smooth, glabrous; leathery, durable. Venation pattern: Pinnate, arcuate. Petiole length: About 1 cm. Petiole diameter: About 3 mm. Color: Developing foliage, upper surface: 179A with random areas of 137B. Developing foliage, lower surface: 179A with random areas of 137C. Fully expanded foliage, upper surface: 11C with random areas of 194A and 147B. Fully expanded foliage, lower surface: 11D with random areas of 191A. Venation, upper and lower surfaces: Same as lamina. Petiole: 144A to 144B.

Flower description:

*Flower type and habit.*—Large single flowers arranged in loose racemes, racemes axillary. About four to five flowers and flower buds per raceme; at full flower, about two or three developing racemes per plant. Flowers face mostly outwardly. Flowers persistent. Flowers not fragrant.

*Natural flowering season.*—Spring until frost in the autumn; flowering continuous.

*Flowering longevity on the plant.*—About one week.

*Flowers.*—Appearance: Single salverform flowers. Diameter: About 5.5 cm. Depth (length): About 6 cm.

*Flower buds* (*just showing color*).—Length: About 2.5 cm. Diameter: About 4 mm. Shape: Ovoid, elongated. Color: 2C; towards apex, 58C.

*Petals.*—Quantity per flower: About five in a single whorl; petals imbricate. Length: About 3 cm. Width: About 2 cm. Shape: Obovate to roughly spatulate. Apex: Acute. Base: Fused. Margin: Entire. Texture, upper and lower surfaces: Smooth, satiny. Color: When opening, upper surface: 58B. When opening, lower surface: 58C to 58D with longitudinal streaks, 155D. Fully opened, upper surface: 58B to 58C. Fully opened, lower surface: 58D with longitudinal streaks, 155D. Throat: 13A. Tube: 58D with longitudinal streaks, 155D; towards the base, 1C streaked with 59D.

*Sepals.*—Quantity: Five per flower in a single whorl; star-shaped calyx. Length: About 8 mm. Width: About 2 mm. Shape: Lanceolate. Apex: Acute. Base: Fused. Margin: Entire. Texture, upper and lower surfaces: Smooth, glabrous. Color, upper surface: 145B. Color, lower surface: 145C.

*Pedicels.*—Length: About 1.7 cm. Diameter: About 2 mm. Angle: About 45° from stem. Strength: Flexible, strong. Color: 145A.

*Reproductive organs.*—Stamens: Quantity per flower: About five adnate to corolla tube and fused around gynoecium. Anther shape: Linear. Anther length: About 8 mm. Anther diameter: About 1.5 mm. Anther color: 10B. Pollen: Scarce. Pollen color: 10B. Pistils: Quantity per flower: One. Pistil length: About 1.7 cm. Stigma color: 1B. Style length: About 1.2 cm. Style color: 1B. Ovary color: 145A.

*Seed/fruit.*—Seed and fruit production has not been observed.

Disease/pest resistance: Plants of the new *Mandevilla* have not been noted to be resistant to pathogens and pests common to *Mandevilla*.

Weather tolerance: Plants of the new *Mandevilla* have been observed to be tolerant to rain and wind and tolerant to temperatures from 0 to 43° C.

It is claimed:

1. A new and distinct cultivar of *Mandevilla* plant named 'Monproud', as illustrated and described.

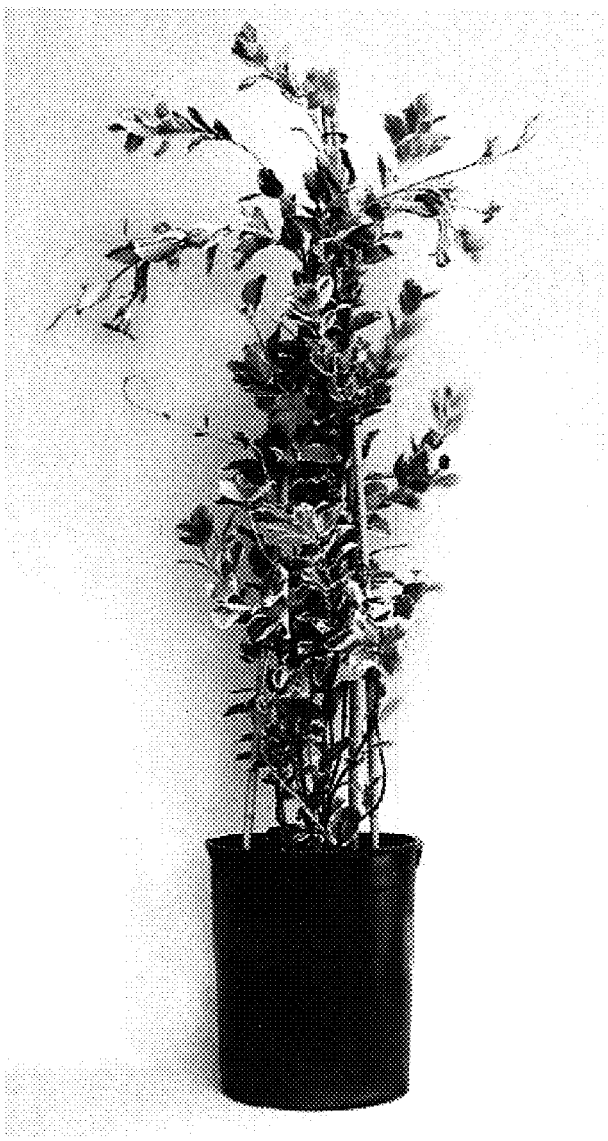
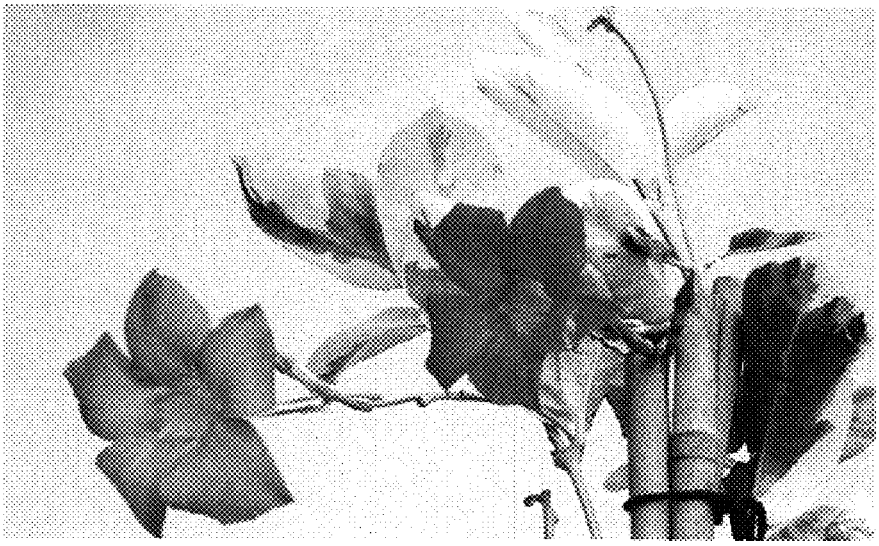

* * * * *